US009158128B2

(12) United States Patent
Pugh et al.

(10) Patent No.: US 9,158,128 B2
(45) Date of Patent: *Oct. 13, 2015

(54) METHODS AND APPARATUS TO FORM ELECTRONIC CIRCUITRY ON OPHTHALMIC DEVICES (71) Applicant: Johnson & Johnson Vision Care, Inc., Jacksonville, FL (US)

(72) Inventors: Randall B. Pugh, Jacksonville, FL (US); Adam Toner, Jacksonville, FL (US); Daniel B. Otts, Fruit Cove, FL (US); James Daniel Riall, Saint Johns, FL (US); Scott R. Humphreys, Greensboro, NC (US); Frederick A. Flitsch, New Windsor, NY (US); Camille Higham, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/781,494

(22) Filed: Feb. 28, 2013

(65) Prior Publication Data

US 2013/0222759 A1      Aug. 29, 2013

Related U.S. Application Data (60) Provisional application No. 61/604,206, filed on Feb. 28, 2012.

(51) Int. Cl.
G02C 7/08      (2006.01)
H01L 23/58     (2006.01)
G02C 7/04      (2006.01)
G02C 7/02      (2006.01)
A61F 2/16      (2006.01)

(52) U.S. Cl.
CPC ....... *G02C 7/04* (2013.01); *G02C 7/022* (2013.01); *G02C 7/083* (2013.01); *H01L 23/58* (2013.01); *A61F 2/1624* (2013.01); *H01L 2924/0002* (2013.01)

(58) Field of Classification Search
CPC ......... G02C 7/081; G02C 7/083; G02C 7/101
USPC ........................................ 351/159.39, 159.4
See application file for complete search history.

(56) References Cited

U.S. PATENT DOCUMENTS 5,657,506 A    8/1997   Pankow
5,918,107 A    6/1999   Fogal et al.
(Continued)

FOREIGN PATENT DOCUMENTS

EP    1760515        3/2007
JP    0561433 A1     3/1993
(Continued)

OTHER PUBLICATIONS

International Search Report for PCT US2013 028318 date of mailing Jun. 7 2013.
(Continued)

*Primary Examiner* — Jordan Schwartz (57) ABSTRACT

This invention discloses an energized Ophthalmic Device with incorporated low energy consuming modes. In some embodiments, media inserts with incorporated low energy consuming modes are described.

21 Claims, 4 Drawing Sheets

(56) References Cited

U.S. PATENT DOCUMENTS

| | | |
|---|---|---|
| 2004/0066898 A1* | 4/2004 | Schick et al. ............... 378/98.9 |
| 2007/0154042 A1 | 7/2007 | Buckley et al. |
| 2009/0033863 A1 | 2/2009 | Blum et al. |
| 2010/0076553 A1 | 3/2010 | Pugh |
| 2010/0110372 A1* | 5/2010 | Pugh et al. ................... 351/177 |
| 2011/0084834 A1 | 4/2011 | Sabeta |
| 2012/0075574 A1* | 3/2012 | Pugh et al. ................... 351/158 |
| 2012/0162600 A1* | 6/2012 | Pugh et al. ............... 351/159.03 |
| 2012/0205714 A1 | 8/2012 | Salcedo et al. |
| 2012/0206691 A1* | 8/2012 | Iwai ........................ 351/159.03 |
| 2012/0235277 A1* | 9/2012 | Pugh et al. ................... 257/532 |
| 2014/0148899 A1* | 5/2014 | Fehr et al. ................... 623/6.22 |

FOREIGN PATENT DOCUMENTS

| | | |
|---|---|---|
| WO | WO 2010/051225 | 5/2010 |
| WO | WO 2011/163080 | 12/2011 |
| WO | WO 2013/130803 A1 | 9/2013 |

OTHER PUBLICATIONS

EP Search Report EP 14 15 9602 Dated Jun. 16, 2014.
SG Search Report for Application No. 10201400573Y Johnson & Johnson informed by Agent Aug. 5, 2015—SG initial Invitation to Respond to Search report and Written Opinion Documents dated Jul. 27, 2015 attached; Actual completion of the Search Report in Singapore Patent Office is Mar. 23, 2015.

* cited by examiner

METHODS AND APPARATUS TO FORM ELECTRONIC CIRCUITRY ON OPHTHALMIC DEVICES

RELATED APPLICATIONS

This application claims priority to Provisional Patent Application No. 61/604,206, filed on Feb. 28, 2012.

FIELD OF USE

This invention describes an energized Ophthalmic Device with an encapsulated Media Insert with a Storage Mode, and more specifically, where the Media Insert incorporates a Switching Mechanism that may be placed in a Storage Mode and in an Operating Mode. The load may control a specific function of the device, such as, for example, optic power adjustment or administration of an active agent. The circuit may be included in an encapsulated Media Insert that may be included in an energized Ophthalmic Device.

BACKGROUND

Traditionally, an Ophthalmic Device, such as a contact lens, an intraocular lens, or a punctal plug, included a biocompatible device with a corrective, cosmetic, or therapeutic quality. A contact lens, for example, may provide one or more of vision correcting functionality, cosmetic enhancement, and therapeutic effects. Each function is provided by a physical characteristic of the lens. A design incorporating a refractive quality into a lens may provide a vision corrective function. A pigment incorporated into the lens may provide a cosmetic enhancement. An active agent incorporated into a lens may provide a therapeutic functionality. Such physical characteristics are accomplished without the lens entering into an energized state. A punctal plug has traditionally been a passive device.

More recently, active components have been incorporated into a contact lens. Some components may include semiconductor devices. Some examples have shown semiconductor devices incorporated in a contact lens placed upon animal eyes. It has also been described how the active components may be energized and activated in numerous manners within the lens structure itself. The topology and size of the space defined by the lens structure creates a novel and challenging environment for the definition of various functionalities. It is important to provide reliable, compact, and cost effective means to interconnect and attach the components upon form factors consistent with the ophthalmic environment.

Including energization elements in an Ophthalmic Device adds the issue of loss of energization between the manufacturing date and the date of actual use of the device. One of the more significant causes of loss of energization may be the leakage of electrical current through devices and structures that connect physically and electrically with the energization elements. Many Ophthalmic Devices, such as disposable contact lenses, have typical shelf lives of six years; hence, there is a need to minimize energization losses by ensuring extremely low leakage current. Therefore, it may be important to ensure that included energization elements and the electrical components they connect to have very low leakages and designed modes of operation that minimize the loss of energization during storage periods. Incorporating the energization elements into the Ophthalmic Device presents the additional issue to current leakage because the solutions to the leakage cannot depend on direct electrical contact.

Technological embodiments that address such an ophthalmological background need may generate solutions that not only address ophthalmic requirements but also encompass novel embodiments for the more general technology space defining energy conservation for encapsulated energized elements.

SUMMARY

Accordingly, the present invention includes an encapsulated Media Insert with a Storage Mode that may be included into an energized Ophthalmic Device, and in some embodiments, specifically, a contact lens. Storage Mode reduces leakage within the Media Insert while operating levels of current are not required. In some embodiments, an energized Ophthalmic Device with a Storage Mode is provided.

The present invention therefore includes disclosure of a Switching Mechanism with a Storage Mode and an Operating Mode, wherein the Switching Mechanism is incorporated into a circuit with at least a load and a power source. For example, the load may control a specific function of the device, such as, for example, optic power adjustment or administration of an active agent. The circuit may be included in an encapsulated Media Insert that may be included in an energized Ophthalmic Device.

The Media Insert may be fully encapsulated to protect and contain the energization elements, traces, and electronic components. The Ophthalmic Device, which may be comprised of a polymeric biocompatible material, may include a rigid center, soft skirt design wherein a central rigid optical element comprises the Media Insert.

In some embodiments, a Storage Mode may be modeled to occur when the Switching Mechanism is modeled to have an increased resistance resulting in a reduced leakage current. This leakage current may meet desired Storage Mode current consumption specifications, and therefore may allow for a substantial shelf life of the energized Ophthalmic Device. Because the Media Insert is fully encapsulated, the Switching Mechanism may be responsive to an outside stimulus that may originate outside the device while not in direct contact with the circuit. Thus, the Switching Mechanism 315 may also be comprised of sensor portions of various kinds. For example, these sensors may be antennas to receive and react to radio frequency emissions as the stimulus, or they may be photocells to react to photon-based outside stimulus.

To further conserve energy, even when the Ophthalmic Device is not in a Storage Mode, a Sleep Mode may be combined with a Storage Mode function.

Whereas a Storage Mode may typically refer to a low energy consumptive state that involves a Switching Mechanism introducing a high resistance into the conductive path of the power source to the load, a Sleep Mode may refer to a low energy consumptive status of electronic circuitry when that circuitry is connected via a low resistance path to the power source.

In some embodiments, a Reset Function may be triggered during the testing process prior to packaging or during the assembly of components themselves. For example, the Reset Function may establish an optimum resting state of the circuit if the device is put into Storage Mode a specified time later. In some embodiments, a block of electronic circuitry may be able to perform the Reset Function and place at least a portion of the load in a predefined energized state.

DETAILED DESCRIPTION OF THE INVENTION

The present invention relates to an energized Ophthalmic Device having a Storage Mode that may conserve energy by reducing current Leakage when the Ophthalmic Device is not being used. In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

An incorporated battery may have a low-leakage state or Storage Mode to maintain enough power to be operational upon use of the Ophthalmic Device. The user of the Ophthalmic Device may then be able to activate or wake up the battery and/or load circuit. Power sources with a Storage Mode may already exist in the electronics field to minimize leakage prior to use of the device, but the issues involved with an energized Ophthalmic Device are distinct from those products currently available. For instance, a common technique in toys to preserve power is to package the product with paper used to cover a coin cell battery. Upon pulling a tab, the paper is removed and contact is made between the battery and circuit. Prior to such activation, the system is in a low-leakage state with long shelf life. Such methods cannot be used for an electronic system encapsulated within a contact lens.

Incorporating the energization elements into the Ophthalmic Device presents additional issues to current leakage because the solutions to the leakage may not depend on direct electrical contact. Therefore, the methods of activation may rely on an outside stimulus whereas the mechanism for switching from storage to active mode could be contained within the energized Ophthalmic Device. This concept is similar to that of a "glow stick" where energy (in the case of a glow stick, a chemical reaction that creates light) is not released until a purposeful event (snapping the slick) activates the device. Unlike a glow stick, an energized Ophthalmic Device with an encapsulated Media Insert may contain complex electronic components and may comprise biocompatible material.

The small space within an ophthalmic Media Insert may add another limitation to a Storage Mode. The area in an ophthalmic Media Insert for all the components of the circuitry including the Switching Mechanism may be 1.5 square millimeters. Size restrictions also limit the possible power supply, and the area used by circuitry may subtract from the area available for the power supply. Accordingly, the range of allowable leakage wherein the energized Ophthalmic Device may still function for practical use after shelf life is very small. The present invention addresses this issue of energy conservation.

Glossary

In this description and claims directed to the presented invention, various terms may be used for which the following definitions will apply:

Encapsulate: as used herein refers to creating a barrier to separate an entity, such as, for example, a Media Insert, from an environment adjacent to the entity.

Energized: as used herein refers to the state of being able to supply electrical current to or to have electrical energy stored within.

Energy: as used herein refers to the capacity of a physical system to do work. Many uses within this invention may relate to the said capacity being able to perform electrical actions in doing work.

Energy Source: as used herein refers to a device or layer that is capable of supplying Energy or placing a logical or electrical device in an Energized state.

Energy Harvester: as used herein refers to a device capable of extracting energy from the environment and converting it to electrical energy.

Functionalized: as used herein refers to making a layer or device able to perform a function including for example, energization, activation, or control.

Leakage: as used herein refers to unwanted loss of energy.

Lens or Ophthalmic Device: as used herein refers to any device that resides in or on the eye. These devices may provide optical correction, may be cosmetic, or may provide functionality unrelated to the eye. For example, the term lens may refer to a contact lens, intraocular lens, overlay lens, ocular insert, optical insert, or other similar device through which vision is corrected or modified, or through which eye physiology is cosmetically enhanced (e.g. iris color) without impeding vision. Alternatively, the Lens may provide non-optic functions such as, for example, monitoring glucose or administrating an active agent. In some embodiments, the preferred lenses of the invention are soft contact lenses are made from silicone elastomers or hydrogels, which include, for example, silicone hydrogels, and fluorohydrogels.

Lens-forming Mixture or Reactive Mixture or Reactive Monomer Mixture (RMM): as used herein refers to a monomer or prepolymer material that may be cured and crosslinked or crosslinked to form an Ophthalmic Device. Various embodiments may include Lens-forming Mixtures with one or more additives such as, for example, UV blockers, tints, photoinitiators or catalysts, and other additives one might desire in an Ophthalmic Devices such as, contact or intraocular lenses.

Lens-forming Surface: as used herein refers to a surface that is used to mold a lens. In some embodiments, any such surface can have an optical quality surface finish, which indicates that it is sufficiently smooth and formed so that a lens surface fashioned by the polymerization of a lens forming material in contact with the molding surface is optically acceptable. Further, in some embodiments, the Lens-forming Surface can have a geometry that is necessary to impart to the lens surface the desired optical characteristics, including without limitation, spherical, aspherical and cylinder power, wave front aberration correction, corneal topography correction and the like as well as any combinations thereof.

Lithium Ion Cell: as used herein refers to an electrochemical cell where Lithium ions move through the cell to generate electrical energy. This electrochemical cell, typically called a battery, may be reenergized or recharged in its typical forms.

Media Insert: as used herein refers to an encapsulated insert that will be included in an energized Ophthalmic Device. The energization elements and circuitry may be incorporated in the Media Insert. The Media Insert defines the primary purpose of the energized Ophthalmic Device. For example, in embodiments where the energized Ophthalmic Device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose or administering an active agent.

Mold: as used herein refers to a rigid or semi-rigid object that may be used to form lenses from uncured formulations. Some preferred Molds include two Mold parts forming a front curve Mold part and a back curve Mold part.

Operating Mode: as used herein refers to a high current draw state where the current over a circuit allows the device to perform its primary energized function.

Optical Zone: as used herein refers to an area of an Ophthalmic Device through which a wearer of the Ophthalmic Device sees.

Power: as used herein refers to work done or energy transferred per unit of time.

Rechargeable or Re-energizable: as used herein refers to a capability of being restored to a state with higher capacity to do work. Many uses within this invention may relate to the capability of being restored with the ability to flow electrical current at a certain rate and for a certain, reestablished time period.

Reenergize or Recharge: as used herein refers to restoring to a state with higher capacity to do work. Many uses within this invention may relate to restoring a device to the capability to flow electrical current at a certain rate and for a certain, reestablished time period.

Reference: as use herein refers to a circuit that produces a fixed and stable voltage or current output suitable for use in other circuits. A reference may be derived from a bandgap, may be compensated for temperature, supply, and process variation, and may be tailored specifically to a particular application-specific integrated circuit (ASIC).

Released from a Mold: as used herein refers to a lens that is either completely separated from the Mold, or is only loosely attached so that it may be removed with mild agitation or pushed off with a swab.

Reset Function: as used herein refers to a self-triggering algorithmic mechanism to set a circuit to a specific predetermined state, including, for example, logic state or an energization state. A Reset Function may include, for example, a power-on reset circuit, which may work in conjunction with the Switching Mechanism to ensure proper bring-up of the chip, both on initial connection to the power source and on wakeup from Storage Mode.

Sleep Mode or Standby Mode: as used herein refers to a low current draw state of an energized device after the Switching Mechanism has been closed that allows for energy conservation when Operating Mode is not required.

Stacked: as used herein means to place at least two component layers in proximity to each other such that at least a portion of one surface of one of the layers contacts a first surface of a second layer. In some embodiments, a film, whether for adhesion or other functions may reside between the two layers that are in contact with each other through said film.

Stacked Integrated Component Devices or SIC Devices: as used herein refers to the products of packaging technologies that assemble thin layers of substrates that may contain electrical and electromechanical devices into operative-integrated devices by means of stacking at least a portion of each layer upon each other. The layers may comprise component devices of various types, materials, shapes, and sizes. Furthermore, the layers may be made of various device production technologies to fit and assume various contours.

Storage Mode: as used herein refers to a state of a system comprising electronic components where a power source is supplying or is required to supply a minimal designed load current. This term is not interchangeable with Standby Mode.

Substrate Insert: as used herein refers to a formable or rigid substrate capable of supporting an Energy Source within an Ophthalmic Device. In some embodiments, the Substrate insert also supports one or more components.

Switching Mechanism: as used herein refers to a component integrated with the circuit providing various levels of resistance that may be responsive to an outside stimulus, which is independent of the Ophthalmic Device.

Energized Ophthalmic Device

Figure 1:
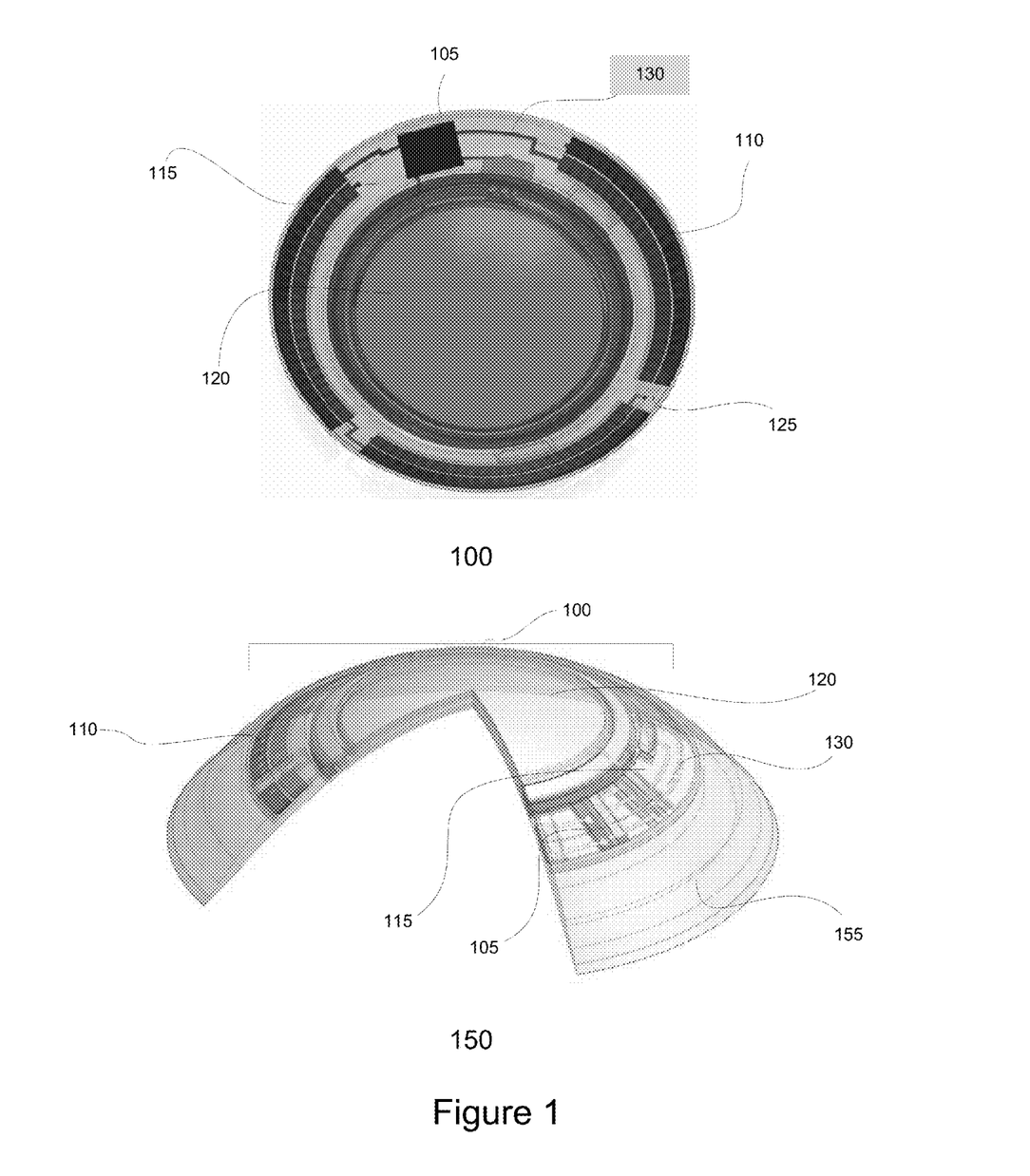
FIG. 1 illustrates an exemplary embodiment of a Media Insert for an energized Ophthalmic Device and an exemplary embodiment of an energized Ophthalmic Device.

Proceeding to FIG. 1, an exemplary embodiment of a Media Insert 100 for an energized Ophthalmic Device and a corresponding energized Ophthalmic Device 150 are illustrated. The Media Insert 100 may comprise an Optical Zone 120 that may or may not be functional to provide vision correction. Where the energized function of the Ophthalmic Device is unrelated to vision, the Optical Zone 120 of the Media Insert 100 may be void of material. In some embodiments, the Media Insert 100 may include a portion not in the Optical Zone 120 comprising a substrate 115 incorporated with energization elements 110 and electronic components 105.

In some embodiments, a power source 110, which may be, for example, a battery, and a load 105, which may be, for example, a semiconductor die, may be attached to the substrate 115. Conductive traces 125 and 130 may electrically interconnect the electronic components 105 and the energization elements 110. The Media Insert 100 may be fully encapsulated to protect and contain the energization elements 110, traces 125 and 130, and electronic components 105. In some embodiments, the encapsulating material may be semipermeable, for example, to prevent specific substances, such as water, from entering the Media Insert 100 and to allow specific substances, such as ambient gasses or the byproducts of reactions within energization elements, to penetrate or escape from the Media Insert 100.

In some embodiments, the Media Insert 100 may be included in an Ophthalmic Device 150, which may comprise a polymeric biocompatible material. The Ophthalmic Device 150 may include a rigid center, soft skirt design wherein a central rigid optical element comprises the Media Insert 100. In some specific embodiments, the Media Insert 100 may be in direct contact with the atmosphere and the corneal surface on respective anterior and posterior surfaces, or alternatively, the Media Insert 100 may be encapsulated in the Ophthalmic Device 150. The periphery 155 of the Ophthalmic Device 150 may be a soft skirt material, including, for example, a hydrogel material.

Figure 2:
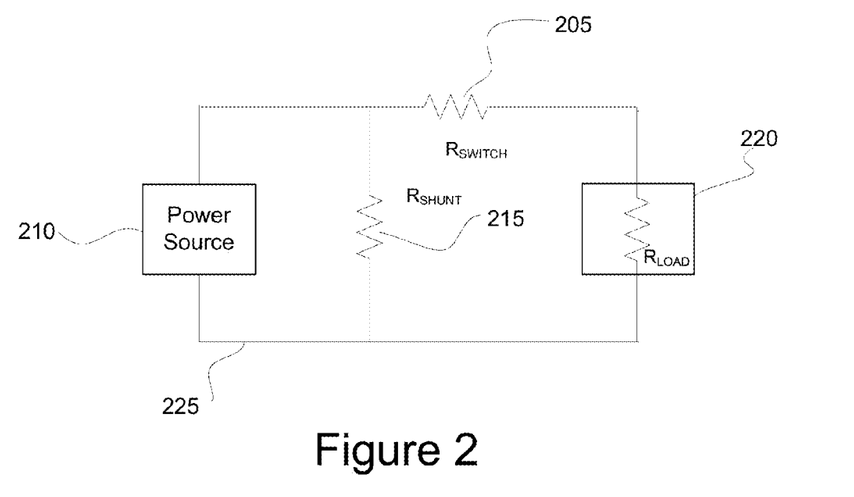
FIG. 2 illustrates a model for the mechanisms of energization loss for devices with energization elements, Power Sources, interconnects, and/or switches.

Proceeding to FIG. 2, a general model for circuit design aspects important in relation to conserving power in energized devices, which may include energized Ophthalmic Devices, is illustrated. Ideally, when the device is in an Operating Mode, the power source 210 may supply the load 220 with full current and without any loss of current to other paths. In realistic conditions however, there are typically parallel leakage paths that may occur in devices, such as, for example, due to leakage within the power source itself or leakage along the interconnections between the power source 210 and the load components 220. The paths of these leakage currents may be modeled as a parallel "Shunt resistance" as shown as a shunt resistor 215. To the extent possible, the leakage paths in the devices are minimized, which would correspond to a model with maximized values of the "Shunt Resistance." Accordingly, preferable embodiments with low leakage may be modeled to have a shunt resistor 225 with very high resistance, such as, for example, $10^9$ ohms.

Even in embodiments where the shunt resistance is very high (and in following discussions assumed to be infinite where the shunt resistor is not included in the circuit illustration), the power source may still have energy drawn from it through the load itself. In some embodiments, a Storage Mode may be modeled to occur when the Switching Mechanism 205 is modeled to have a varying resistance. In ideal cases, the resistance across the Switching Mechanism 205 may be zero when the circuit 225 is in an Operating Mode and infinite when the circuit 225 is in a Storage Mode. In some exemplary embodiments, the Switching Mechanism may add minimal resistance, such as, for example, less than 10 ohms, when the Switching Mechanism 205 is closed, and add very high resistance, such as, for example, $10^9$ ohms, when the Switching Mechanism 205 is open. In some embodiments, to meet this specification, the circuit may be inactive in a Storage Mode. For example, some embodiments may include a high-isolation switch that may shut the battery off from the load, where the load may include, for example, a reference, oscillators, a digital logic circuits, or in some embodiments a lens driver circuit.

In an energized Ophthalmic Device, the load 220 may control a specific function of the device, such as, for example, optic power adjustment or administration of active agents. In some preferable embodiments, the load resistance may be nominal. The previously described examples for current, power, and resistance may be within the normal operating boundaries that apply in some exemplary embodiments. For example, in some preferable embodiments, the current draw when the energized Ophthalmic Device is in a Storage Mode, which may be classified as the leakage current, may be less than 400 pA.

This leakage current may meet desired Storage Mode current consumption specifications and therefore may allow for a substantial shelf life of the energized Ophthalmic Device. In some embodiments, for example, the level of leakage while the Ophthalmic Device is in a Storage Mode may be at a targeted level, which may give an added benefit of limiting the wear on the components of the circuit.

In some preferable embodiments, when the energized Ophthalmic Device is in an operating mode, the current may be 3 uA or less on average but may contain peaks to 10 milliamps or more. $I_{OPERATING\ MODE}$ may be the current after the energized Ophthalmic Device has been woken up from storage, and $I_{STORAGE\ MODE}$ may be the non-operating leakage current while the device is in Storage Mode and may directly affect the potential time the device may operate at its $I_{OPERATING\ MODE}$.

In energized Ophthalmic Devices that do not have a Storage Mode, the available power from the energization elements after years of storage might steadily decrease, potentially to a de-energized state of zero available power. By adding a Storage Mode aspect to components or to the device design, the resulting device may be modeled as having a Switching Mechanism 205 with a high $R_{SWITCH\ OPEN}$ that may mitigate the current loss over time. The time at which an active circuit may operate at a given $I_{OPERATING\ MODE}$ may be directly related to the $R_{SWITCH\ OPEN}$ of the model Switching Mechanism 205 in that a higher $R_{SWITCH\ OPEN}$ may reduce the leakage draw on the energization element, which may then allow for a longer time that the device may operate at its $I_{OPERATING\ MODE}$. In another sense, when the device is operating it may be important that the current flowing through the modeled Switching Mechanism not cause effects within that mechanism itself; therefore, in some embodiments, the Switching Mechanism 205 may be comprised of a material that, when closed, may withstand currents up to and including the $I_{OPERATING\ MODE}$ over the expected periods of operation.

There may be a variety of design parameters that relate to the type, dimension, and quantity of energization cells that are utilized for a particular application. In some embodiments, for example, the power source 210 may be comprised of two battery cells in series each having a cell voltage of between 0.8 to 1.65V thus providing a voltage supply of 1.6 to 3.3V. The desire to configure cells of this type into this voltage range may be related to the technology that is utilized in the electronic circuitry as it may operate in a window around this electrical potential. If different types of battery are used, for example, where the chemistry involved in the anodes and cathodes is varied, the nominal cell voltages may shift.

Within a certain battery type, the size of the batteries employed may be related to the electrical current phenomena that have been discussed herein. For example, a particular application may have a targeted operating life at a certain operating current. Based on this target value alone, the size requirements of the cells may simply be estimated from the inherent energy density of the cells and the required energy for the operating life. However, as has been described herein, the situation may typically be more complicated since the energy required for the storage life might also factor into the size requirement of the cells as well. The energy required for storage life is a significant function of $I_{STORAGE\ MODE}$. Thus, it may be clear why minimization of $I_{STORAGE\ MODE}$ is desirable because it either reduces the amount of battery chemicals required for an application, or on the other hand, increases the operating life parameters for a given size of available space for batteries in an application.

By reducing leakage and limiting the energy flow through the circuit, a Storage Mode may also minimize the byproducts that may result from reactions caused by an energized circuit. This may be particularly significant in embodiments where the Ophthalmic Device is shipped in small, sealed packages, such as, for example, blisters, where even a small accumulation of byproducts may be damaging to the integrity of the Ophthalmic Device.

To further conserve energy, even when the Ophthalmic Device is not in a Storage Mode, a Sleep Mode may be combined with a Storage Mode function. Whereas a Storage Mode may typically refer to a low energy consumptive state that involves a Switching Mechanism introducing a high resistance into the conductive path of the power source to the load, a Sleep Mode may refer to a low energy consumptive status of electronic circuitry when that circuitry is connected via a low resistance path to the power source. Such a Sleep Mode may occur when the connected electronic circuitry controls itself to essentially "turn off" most of its circuitry, for example to save energy by waiting to perform sensor sampling at a predetermined rate.

Figure 3:
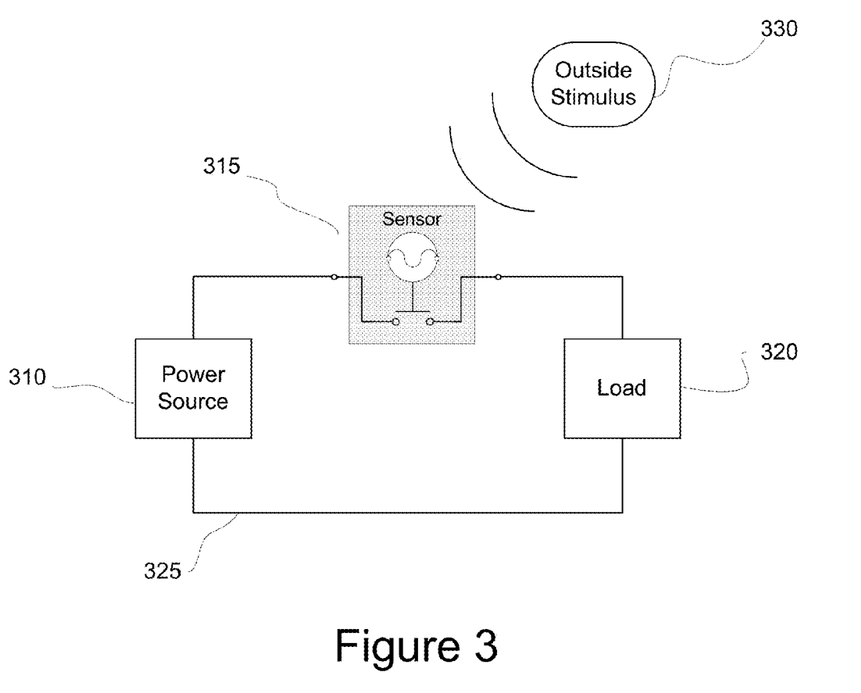
FIG. 3 illustrates an exemplary embodiment of a circuit design for an energized device with an externally activated Storage Mode, which may be included in Ophthalmic Devices with encapsulated Media Inserts.

Proceeding to FIG. 3, an exemplary embodiment of a circuit design for a device with a Storage Mode is illustrated. The circuit 325 may include a power source 310 and a load 320 that may control a specific function of the Ophthalmic Device. As mentioned previously, the parasitic leakages of the power source 310 itself and of the connections between the power source 310 and the load 320 may be designed and manufactured to be very small and thus no "shunt resistance" is depicted for example. In some embodiments, a Switching Mechanism may be placed in series with the power source 310 and the load 320 to facilitate a storage mode.

The Switching Mechanism 315 may be responsive to an outside stimulus 330 not in direct contact at its origination with the circuit 325. The Switching Mechanism 315 is depicted generally as a device that is sensitive and reactive to the outside stimulus 330. Thus, the Switching Mechanism 315 may also be comprised of sensor portions of various kinds. For example, these sensors may be antennas to receive and react to radio frequency emissions as the stimulus, or they may be photocells to react to photon-based outside stimulus. There may be numerous types of sensors inherent to a switch being sensitive to an outside stimulus. In other embodiments, the detection of the outside stimulus may involve a physical change of some kind to an element in the switch. For example, exposure of elements in the switch to a thermal stimulus from outside the lens may physically change the resistivity of a component within the switch and cause a reaction much as the other described sensor elements could. Some embodiments may be sensitive to sound as well.

In some embodiments, for example, control of the Switching Mechanism 315 may use electronic means, mechanical means, or magnetic means. For example, electronic means may involve transistor circuitry in the switching, mechanical means may involve metallic contacts in the switching, and magnetic means may involve reed relays. There may be numerous switches that will have high resistance when in an off mode and low resistance in an on mode.

Some embodiments may include a Switching Mechanism 315 that may repeatedly be placed in a Storage Mode and an Operating Mode, which may allow, for example, testing during manufacturing or repeated use of the Ophthalmic Device. In some such embodiments, the load 320 may also control the Switching Mechanism 315, allowing the load 320 to place the Switching Mechanism 315 back into a Storage Mode. The load 320 may contain additional sensors, such as, for example, an infrared link, which may receive commands from a user or some other passive outside stimulus. Upon reception of a shutdown command, the load 320 may activate the Switching Mechanism.

In some embodiments, for example, the circuit may be comprised of multiple Switching Mechanisms, not shown, that may independently be activated for a single use, which may allow for a specific number of uses. In such embodiments, after a single use, the load may place one of the Switching Mechanism into Storage Mode so that the Ophthalmic Device may be activated again with minimal leakage while not in use. In some alternative embodiments, such as with single daily use devices, the Switching Mechanism may be placed in a Storage Mode and activated to an Operating Mode one time.

A Storage Mode may allow for reliable shipping methods because the Ophthalmic Device may be kept in a known off state. In some embodiments, a Storage Mode alone may be sufficient in establishing a stable state for shipping. In other alternative embodiments, a Reset Function may be triggered during the testing process prior to packaging or during the initial assembly of the components into the device. For example, the Reset Function may establish an optimum resting state of the circuit if the device is put into Storage Mode a specified time later. In some embodiments, this specified time may be shorter after testing than after user activation thereby allowing two Reset Functions, one for shipping and one for use. In some embodiments, a block of electronic circuitry may be able to perform the Reset Function and place at least a portion of the load 320 in a predefined energized state. The block of electronic circuitry may be incorporated within the circuit, including, for example, within the load 320.

Figure 4:
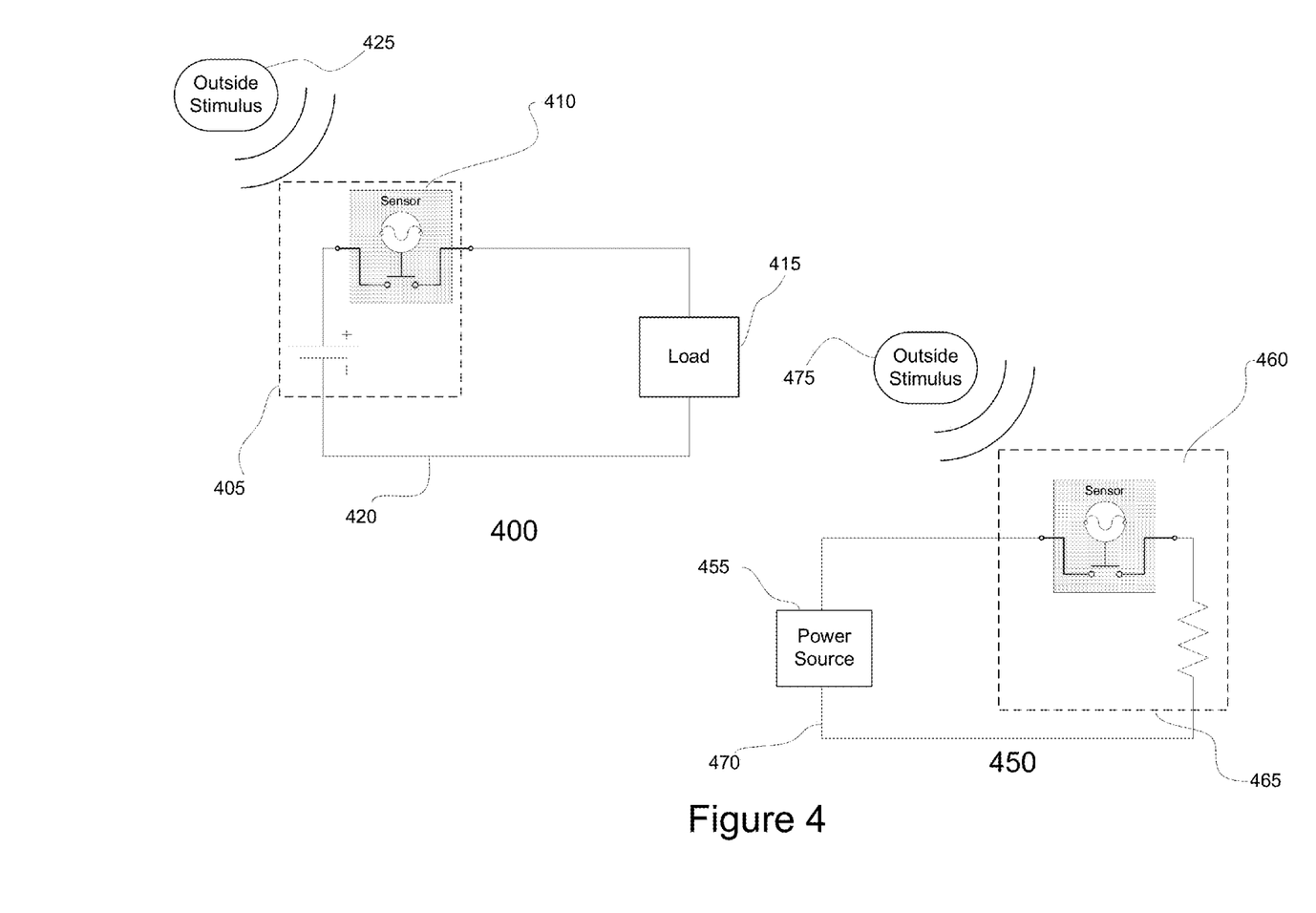
FIG. 4 illustrates alternate embodiments of circuit designs for energized devices with externally activated Storage Modes, which may be included in Ophthalmic Devices with encapsulated Media Inserts.

Proceeding to FIG. 4, alternative embodiments of a circuit design for an energized device with a Storage Mode are illustrated, and such circuits may be incorporated into Ophthalmic Devices. In some embodiments of the circuit design 400, the Switching Mechanism 410 may be integrated within the power source 405, which then may be placed in the circuit 420 in series with the load 415. In some alternative embodiments of a circuit design 450, the Switching Mechanism 460 may be integrated within the load 465. The load 465 may be placed in the circuit 470 in series with the power source 455. In these embodiments 400 and 450, the Switching Mechanism 410 may be responsive to an outside stimulus 425 and 475.

Figure 5:
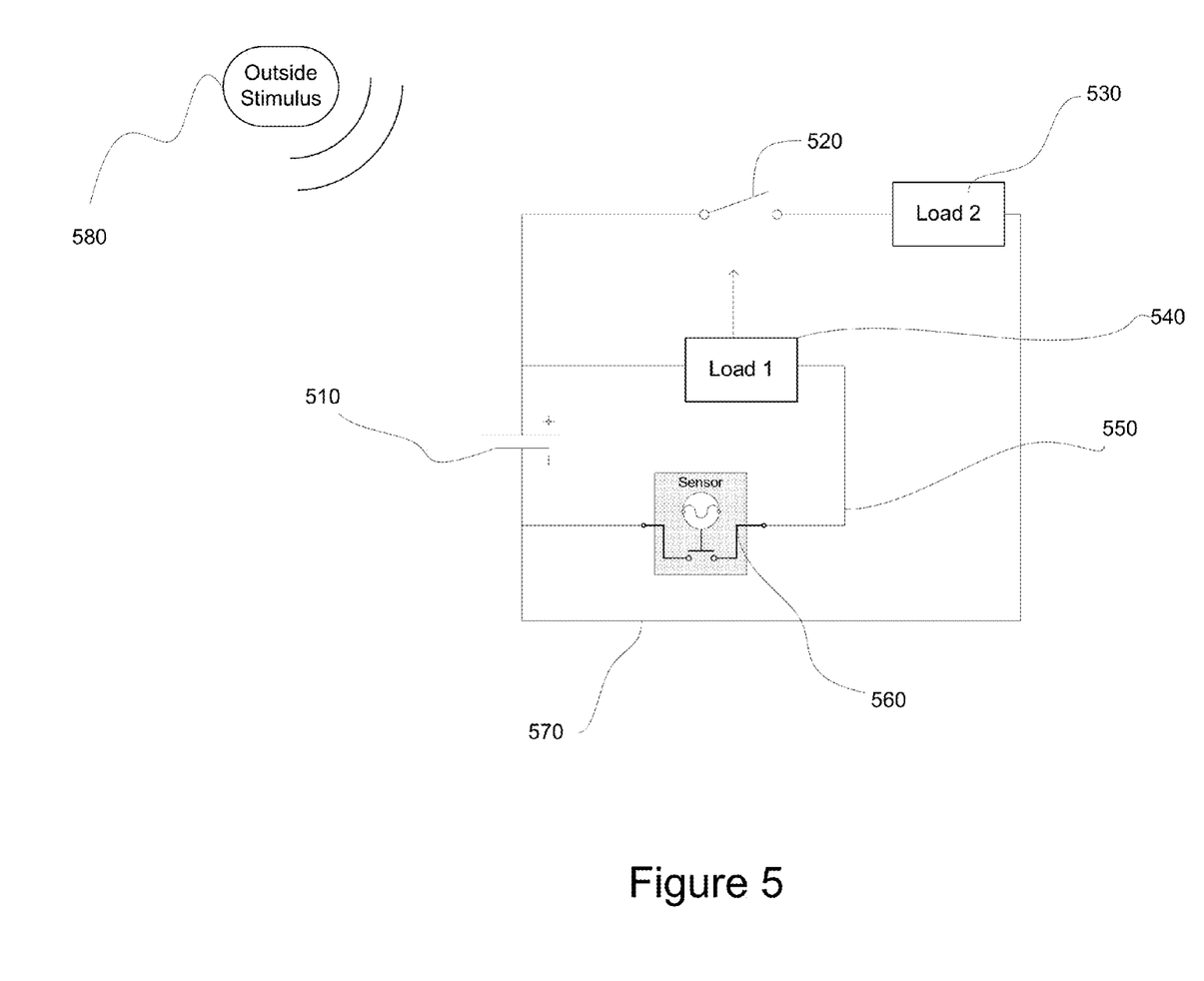
FIG. 5 illustrates an exemplary embodiment of a circuit design for an energized device with a Storage Mode wherein a Switching Mechanism important to the state of the Storage Mode is itself comprised of a separate load and switch, which may be included in Ophthalmic Devices with encapsulated Media Inserts.

Proceeding to FIG. 5, an embodiment where the primary Switching Mechanism 550 is a discrete circuit is illustrated. The primary Switching Mechanism 550 may be comprised of a load 540 separate from the controlling load 530 that may operate the energized Ophthalmic Device. In some embodiments, the primary Switching Mechanism 550 may operate at a very low power to constantly sample for the outside stimulus 580. By utilizing power from the source 510, the primary Switching Mechanism 550 may provide benefits over a passive Switching Mechanism, for exampling having greater sensitivity or selectivity to external stimulus.

Upon activation by an outside stimulus 580, the switching load 540 may control a switch 520 that may be in the main circuit 570 in series with the controlling load 530 and the power source 510. In some embodiments, when the main switch 520 is activated, the main circuit 570 may operate at a high power, such as, for example, 3 uA average and 10 mA peak. In some embodiments, the main switch 520 may further be controlled by the load 540, which may place the switch 520 back in a Storage Mode.

The primary Switching Mechanism 550, in some embodiments, may include an additional Switching Mechanism 560. This additional Switching Mechanism 560 may provide many functions, such as, for example, further reducing current leakage and protecting the power components. In some embodiments, the additional Switching Mechanism 560 may only be activated once the Media Insert is incorporated in the energized Ophthalmic Device and the device is ready to be packaged. This may protect the circuitry from damage that may be caused by subsequent manufacturing procedures, including, for example, curing lights used to set the hydrogel. In some embodiments, the additional Switching Mechanism 560 and the primary Switching Mechanism 550 may also be responsive to different types of outside stimulus 580.

For example, in some embodiments, the additional Switching Mechanism 560 may be responsive to temperature, and the primary Switching Mechanism 550 may be responsive to ambient light. Such embodiments may allow the energized Ophthalmic Device to be stored in a cool or cold temperature while in the most conservative stage of a Storage Mode. Once the energized Ophthalmic Device is exposed to warmer temperatures, the additional Switching Mechanism 560 may trigger the primary Switching Mechanism 550 to begin sampling in low power for ambient light, while still keeping the main circuit 570 in a Storage Mode. Upon exposure to ambient light, the primary Switching Mechanism 550 may close the main switch 520 and trigger an Operating Mode.

This combination of temperature and light is for exemplary purposes only, and it may be apparent to those ordinarily skilled in the art that other combinations of switching systems may be practical. The combination of the primary Switching Mechanism and additional Switching Mechanism may include, for example, electrical, mechanical, or magnetic systems and may depend on stimuli such as, for example, electromagnetic emissions, sound, temperature, or light.

The invention claimed is:

1. An energized ophthalmic device comprising:
an electrical power source incorporated in a media insert;
an electrical load;
an electrical connection medium for placing the electrical load in electrical communication with the electrical power source, wherein the electrical power source and the electrical load comprise a portion of a circuit; and
a first switching mechanism included in the circuit comprising a plurality of modes including at least an operating mode and a first storage mode,
wherein the first storage mode places the energized ophthalmic device into a lower energy consuming state than the operating mode,
wherein the first switching mechanism adds resistance to restrict current flow through the electrical load when the energized ophthalmic device is in the first storage mode, and
wherein the first switching mechanism is sensitive to a first stimulus originating external to the energized ophthalmic device.

2. The energized ophthalmic device of claim 1, wherein the first switching mechanism is included within the electrical power source.

3. The energized ophthalmic device of claim 1, wherein the first switching mechanism is included within the electrical load.

4. The energized ophthalmic device of claim 1, wherein the first switching mechanism is external to the electrical power source and the electrical load.

5. The energized ophthalmic device of claim 1, further comprising: a second switching mechanism integrated with the first switching mechanism, wherein the second switching mechanism controls the first switching mechanism and is sensitive to a second stimulus originating outside of the energized ophthalmic device.

6. The energized ophthalmic device of claim 5, wherein the first stimulus and the second stimulus originate from different sources.

7. The energized ophthalmic device of claim 1, further comprising: a first block of electronic circuitry within the electrical load configured to perform a first reset function upon at least a first portion of the electrical load, when activated, to place the first portion of the electrical load in a predefined energized state.

8. The energized ophthalmic device of claim 7, wherein the first reset function is performed when the first switching mechanism is taken out of the first storage mode.

9. The energized ophthalmic device of claim 7, wherein the first reset function is performed during assembly when connections included in the circuit are formed.

10. The energized ophthalmic device of claim 1 further comprising: a block of circuitry able to invoke a standby mode in order to conserve energy by reducing current flow through the circuit when the operating levels are not required.

11. The energized ophthalmic device of claim 10, wherein the electrical load further comprises a sensor sensitive to a second stimulus originating outside the energized ophthalmic device.

12. The energized ophthalmic device of claim 1 further comprising: a switch incorporated within the circuit, wherein the switch is sensitive to an internal stimulus originating from the first switching mechanism, wherein the first switching mechanism is a discrete circuit.

13. A media insert comprising:
an electrical power source;
a load in connection with the electrical power source, wherein the electrical power source and the load comprise at least a portion of a circuit; and
at least a one switching mechanism comprised within a portion of the circuit, wherein the switching mechanism has a plurality of modes including at least an operating mode and a storage mode,
wherein the storage mode places the media insert in a lower energy consuming state than the operating mode,
wherein the switching mechanism adds resistance to minimize current flow through the circuit when the media insert is in the storage mode,
wherein the switching mechanism allows the current flow in the circuit to increase in the operating mode, and
wherein the switching mechanism is sensitive to a stimulus originating outside of the media insert.

14. An energized ophthalmic device comprising:
an electrical power source incorporated in a media insert;
an electrical load;
an electrical connection medium for placing the electrical load in electrical communication with the electrical power source, wherein the electrical power source and the electrical load comprise a portion of a circuit;
a first switching mechanism included in the circuit comprising a plurality of modes including at least an operating mode and a first storage mode; and
a second switching mechanism integrated with the first switching mechanism and controlling the first switching mechanism,
wherein the first storage mode places the energized ophthalmic device into a lower energy consuming state than the operating mode,
wherein the first switching mechanism permits a current to flow through the electrical load,
wherein the first switching mechanism adds resistance to restrict current flow through the electrical load when the energized ophthalmic device is in the first storage mode,
wherein the first switching mechanism is sensitive to a first stimulus originating external to the energized ophthalmic device and the second switching mechanism is sensitive to a second stimulus originating outside of the energized ophthalmic device, and
wherein the first stimulus takes the first switching mechanism out of the first storage mode and the second stimulus takes the second switching mechanism out of a second storage mode.

15. The energized ophthalmic device of claim 14, wherein taking the second switching mechanism out of the second storage mode allows for less current flow than allowed by taking the first switching mechanism out of the first storage mode.

16. The energized ophthalmic device of claim 15, wherein taking the second switching mechanism out of the second storage mode allows for a periodic sampling to detect the first stimulus.

17. An energized ophthalmic device comprising:
an electrical power source incorporated in a media insert;
an electrical load;
an electrical connection medium for placing the electrical load in electrical communication with the electrical power source, wherein the electrical power source and the electrical load comprise a portion of a circuit;

a switching mechanism included in the circuit comprising a plurality of modes including at least an operating mode and a storage mode; and a first block of electronic circuitry within the electrical load configured to perform a first reset function upon at least a first portion of the electrical load, when activated, to place the first portion of the electrical load in a predefined energized state, wherein the storage mode places the energized ophthalmic device into a lower energy consuming state than the operating mode, wherein the switching mechanism permits a current to flow through the electrical load, wherein the switching mechanism adds resistance to restrict current flow through the electrical load when the energized ophthalmic device is in the storage mode, wherein the switching mechanism is sensitive to a stimulus originating external to the energized ophthalmic device, wherein the first reset function is performed when the switching mechanism is taken out of the storage mode, and wherein the predefined energized state is optimized for an initial placement of the energized ophthalmic device in or on an eye.

18. The energized ophthalmic device of claim 17 further comprising: a second block of electronic circuitry within the electric load configured to perform a second reset function upon a second portion of the electric load, when activated, to place the second portion of the electrical load in a predefined energized state.

19. The energized ophthalmic device of claim 18, wherein the second reset function is performed when the switching mechanism is taken out of the storage mode for use.

20. An energized ophthalmic device comprising:
an electrical power source incorporated in a media insert;
an electrical load;
an electrical connection medium for placing the electrical load in electrical communication with the electrical power source, wherein the electrical power source and the electrical load comprise a portion of a circuit; and
a switching mechanism included in the circuit comprising a plurality of modes including at least an operating mode and a storage mode,
wherein the storage mode places the energized ophthalmic device into a lower energy consuming state than the operating mode,
wherein the switching mechanism permits a current to flow through the electrical load,
wherein the switching mechanism adds resistance to restrict current flow through the electrical load when the energized ophthalmic device is in the storage mode,
wherein the switching mechanism is sensitive to a stimulus originating external to the energized ophthalmic device, and
wherein the electrical load controls switching the switching mechanism from the operating mode to the storage mode.

21. An energized ophthalmic device comprising:
an electrical power source incorporated in a media insert;
an electrical load;
an electrical connection medium for placing the electrical load in electrical communication with the electrical power source, wherein the electrical power source and the electrical load comprise a portion of a circuit;
a switching mechanism included in the circuit comprising a plurality of modes including at least an operating mode and a storage mode;
a block of circuitry able to invoke a standby mode in order to conserve energy by reducing the current flowing through the circuit when the operating levels are not required; and
a plurality of single use switching mechanisms,
wherein the storage mode places the energized ophthalmic device into a lower energy consuming state than the operating mode,
wherein the switching mechanisms permit a current to flow through the electrical load,
wherein the switching mechanisms add resistance to restrict current flow through the electrical load when the energized ophthalmic device is in the storage mode,
wherein the switching mechanisms are sensitive to a stimulus originating external to the energized ophthalmic device,
wherein each of the single use switching mechanisms may be individually taken out of a storage mode,
wherein the electrical load may individually place each of the single use switching mechanisms into a storage mode, and
wherein taking a first single use switching mechanism out of a storage mode allows the current to flow through the circuit and placing a second single use switching mechanism into a storage mode reduces the current flow through the circuit.

* * * * *